United States Patent [19]

Meyer

[11] Patent Number: 4,901,710
[45] Date of Patent: Feb. 20, 1990

[54] LEG RESTRAINT

[76] Inventor: Paul A. R. Meyer, 94 Blinco Grove, Cambridge, United Kingdom

[21] Appl. No.: 21,772

[22] Filed: Mar. 4, 1987

[30] Foreign Application Priority Data

Mar. 5, 1986 [GB] United Kingdom ................. 8605472

[51] Int. Cl.$^4$ .............................................. A61F 5/04
[52] U.S. Cl. .................................. 128/78; 128/80 A; 128/87 C
[58] Field of Search .................... 128/134, 80 R, 80 A, 128/80 B, 80 F, 84 R, 84 A, 85, 87 R, 88, 83.5

[56] References Cited

U.S. PATENT DOCUMENTS

| 3,730,177 | 5/1973 | Thum | 128/80 A |
| 4,481,941 | 11/1984 | Rolfes | 128/87 R |
| 4,497,315 | 2/1985 | Fettweis et al. | 128/80 A X |
| 4,574,790 | 3/1986 | Wellershaus | 128/80 A X |

FOREIGN PATENT DOCUMENTS

| 1263219 | 3/1968 | Fed. Rep. of Germany . |
| 2714272 | 11/1979 | Fed. Rep. of Germany . |
| 3508844 | 9/1986 | Fed. Rep. of Germany ... 128/80 A |

Primary Examiner—Robert A. Hafer
Assistant Examiner—Kevin G. Rooney

[57] ABSTRACT

An orthopaedic device which is suitable for the treatment or prevention of subluxation or dislocation of the hip joint is described. The device comprises a waist band, two thigh bands and two leg bars. Each leg bar is attached at one end to a thigh band which is free to rotate about an axis which is perpendicular to the leg bar. The other end of each leg bar is rotatably held in a sleeve attached to the waist band. Each sleeve is capable of being inclined downwards with respect to the plane of the waist band. The spacial relationship of the axis of the sleeve and the distal end of the leg bar is such that the device operates by maintaining the legs of the wearer in abduction that is appropriate to the extent of hip flexion by altering the separation of the legs in a smooth and controlled way during hip flexion.

11 Claims, 4 Drawing Sheets

LEG RESTRAINT

The invention relates to an orthopaedic device which is suitable for the treatment or prevention of subluxation or dislocation of the hip joint. The device operates by maintaining the legs of the wearer in abduction that is appropriate to the extent of hip flexion by altering the separation of the legs in a smooth and controlled way during hip flexion.

Posterior subluxation or dislocation of the hip in childhood is favoured by laxity of the joint ligaments and excessive adduction and internal rotation of the leg. The former situation predominates in congenital dislocation of the hip (CDH) and the latter in children with cerebral palsy. Among patients with cerebral palsy two sub-groups arise: those in whom excessive adduction and internal rotation accompanies exercise (particularly attempts to bear weight and walk), and those in whom the dislocating force is present continuously as a result of spasticity.

The aim of most known remedial devices that are used to manage this problem is to overcome the dislocating forces by splinting the legs in abduction and flexion. With time the joint then becomes more stable as a result of deepening of the acetabulum and tightening of the joint ligaments.

Immobilisation of the hip joint may be acceptable for brief periods in young infants with CDH. Even for this condition some attempts have been made to permit limited movement (see for example U.S. Pat. No. 4497315, German Offenlegungsschrift No. 2714172 and U.K. Pat. No. 1343850). However, in older children with hip instability the largest possible range of movement is desirable, not least because weight-bearing stimulates acetabular development. In patients with hip subluxation resulting from neurological abnormalities, hard-won patterns of movement may be lost by prolonged immobilisation.

If patients with unstable hips are to be allowed substantial movement, including weight-bearing and walking, a device must be provided that overcomes the dislocating forces in all positions of hip flexion. It should offer maximum abduction in hip flexion, but this must be reduced during hip extension in order to permit weight-bearing. The legs should be able to move independently. Such a device does not exist and the proposed invention is intended to fill that hiatus.

Accordingly the present invention provides an orthopaedic device which comprises a waist band, two thigh bands and two leg bars in which one end of each of the leg bars is attached to a thigh band which is free to rotate about an axis perpendicular to the leg bar, the other end of each leg bar being held in a sleeve attached to the waist band, each sleeve being capable of being inclined downwards with respect to the plane of the waist band, and the leg bars make an obtuse angle with the axis of sleeve, so that when worn the separation of the leg bars is less when the legs are extended than when they are flexed and in which each leg bar is adapted so that when worn each leg bar is parallel to the leg of the wearer.

Aptly the axis of the sleeve is inclined downwards and suitably may make an angle ($\gamma$) with the vertical of less than 90°, more aptly of between 40° and 80°, and preferably between 50° and 70°, for example 60°. In order that leg abduction should vary with hip flexion upon rotation of the leg bar in the sleeve, the angle between the leg bar and the sleeve is aptly less than 90° and suitably between 30° and 60°, and preferably is between 40° and 50°, for example 45°.

A distinguishing feature which differentiates the device of the present invention from those of the prior art is the use of an inclined sleeve in order to vary leg abduction with hip flexion. Conveniently, the range of abduction required from the device is virtually the same regardless of the size of the patient or the pathology present. The sleeve may be of any form which has an axis about which the leg bar may rotate and which is inclined downwards from the plane of the waist band. Suitably the sleeve may comprise of a hollow tube attached to the waist band with its axis inclined downwards and holding one end of a leg bar in a manner which permits rotation of the leg bar about the axis of the hollow tube that is the leg bar and hollow tube are concentric. The device will normally contain two such sleeves.

The sleeves may be attached in a fixed relationship with the waist band for example by using screws or fixing bolts. However, it is preferred if the angle of inclination of the sleeves could be varied so as to suit any particular patient or stage of treatment, that is for both from patient to patient and during therapy. The sleeves may be altered together for example if the end of each pivot has a hole which is threaded by the same bolt, which is in turn movable vertically and lockable in a slot in the waist band. Alternatively the sleeves may be independently movable for example by each carrying a slotted plate at one end which may be locked in any inclined position by a fixing bolt passing through the slot to the waist band. The waist band may be reinforced, for example with a metallic plate, and the sleeves attached to the reinforcement.

In an alternative embodiment the angle of inclination may be varied continuously for example by a pinion on the end of each leg bar engaging a rack on the waist band.

In a special case the sleeve axis may be temporarily horizontal (allowing full rotation at the hip, but unvarying abduction) and may be locked in this position for use as a night splint or in the early stages of post-operative treatment. Variable angle embodiments of the present invention are capable of providing this facility but it is preferred and is normal for use if the axis of the sleeve is inclined downwards.

The angle between the axis of the sleeve and the saggital plane determines the degree of hip extension at which minimum leg abduction occurs. If this is to be below the centre of gravity, the sleeve axis should be angled forwards slightly suitably at an angle of less than 20°, preferably between 10° and 15°, since the waist band is tilted forwards when worn.

The arc of rotation of the leg bars may be restricted when they rotate within their respective sleeves, for example by providing a pin on the leg bar which moves between the ends of a slot in the sleeve. The ability to vary the angle and amplitude of rotation of the leg bars may facilitate the gradual acquisition of hip stability in children with cerebral palsy.

The locking of the leg bars against rotation within the sleeve may be desirable at night (in hip flexion and maximum abduction) or to stabilise the hips while the child stands (in hip extension) or while the child sits (in hip flexion). In children with CDH continual immobilisation in hip flexion may be required. However it is preferred that during normal use the leg bars are able to rotate freely. The leg bar may be locked within the sleeve using a locking nut, a clamp device or a ratchet type device.

The sleeve may also be spring loaded to provide a continuous abducting force to help to overcome spastic adductor tone.

The leg bars are adapted so that the part of the leg bar at one end of which is the thigh band is parallel to the legs. To achieve this each leg bar may contain two bends. The first bend is a simple bend downwards from the axis of the sleeve. The second bend is at a compound angle which brings the leg bar forwards and obliquely outwards so that it lies adjacent to the lateral thigh in use. Alternatively for more subtle adjustments, one or both bends could comprise a clampable hinge or a multi-jointed bar clamped by an axial tension wire.

The leg bars may be retained within their sleeves so that they may rotate therein. In one form of retaining means the end of the leg bar which is within the sleeve has a plurality of transverse grooves, for example 3, and is retained within the sleeve by means of a spring that registers with one of these grooves. By placing the spring in different grooves the separation of the leg bars may be varied.

Efficient abduction of the leg bars during hip flexion relies upon the waist band remaining in a fixed coronal plane. In practice this means that an upwards force acts upon the abdomen and a downwards force acts upon the sacrum. In order to reduce the pressure at these points, expansions of the waist band may be provided. Such a sacral expansion has the additional effect of preventing any rotation resulting from assymetrical muscle tone, since it cannot pass the iliac crest. Aptly the abdominal expansion is in the form of an anterior pressure pad that may pivot at both its connections with the main waist band.

The anterior pressure pad should be of a sufficiently size to distribute over the ribs and upper abdomen the upward force imposed by attempted leg adduction. The posterior expansion should distribute the contrary downward force over the pelvis and prevents rotation of the band. However, the exact shape of the waist band may take many forms: for example it may be cushioned or moulded to suit each individual child, it may be attached to a harness which passes over the shoulders of the wearer or it may be in the form of a bucket in which the child sits.

Both thigh bands are preferably padded and attached to the leg bars. They may be free to rotate about a chosen axis that is perpendicular to the leg bars and angled medially and anteriorly. Hip flexion and abduction of the leg bar results in external rotation of the thigh band, which opposes the (dislocating) force of the muscles of internal rotation.

When the angle of inclination of the sleeve is adjustable, it is desirable that it is also possible to alter the axis of rotation of the thigh band around the leg bar.

The thigh bands may be expanded to enclose or parallel the whole thigh, and may be attached to the leg bars close to the pivot point.

It may be appropriate for the thigh band to follow only part of the circle described by the end of the leg bar. Rotation would be permitted in the axis of the leg bar and restricted to a chosen arc by stops.

The waist band and thigh bands are suitably formed from a polymer which is mouldable under the influence of heat. Suitable polymers include polyolefins and particularly preferred is polypropylene.

Both the waist band and thigh bands may carry padding material which will lie between the polymer of the band and the skin when the device is worn. Suitable padding material includes non-woven surgical padding for example of the type which is often present beneath plaster casts or a resilient foam such as a resilient polyurethane foam.

Both the waist band and thigh bands may carry means to restrain the bands in position. In the case of the waist band this is the anterior pressure pad as herein described and the thigh bands may be restrained by means of a conventional belt and buckle.

The leg bars are suitably formed from a metal such as steel.

This device achieves leg abduction which is maximum during hip flexion and lessens during extension. Between these extremes of position the separation of the legs is altered in a smooth and controlled way. The user may stand, walk, sit and sleep while the hip joint remains correctly positioned. No previous device has permitted this range of movement while ensuring hip stability. Preferred embodiments of an orthopaedic device of the present invention will now be described with reference to the following drawings in which FIG. 1 shows the relationship of the device to the pelvis.

Figure 1:
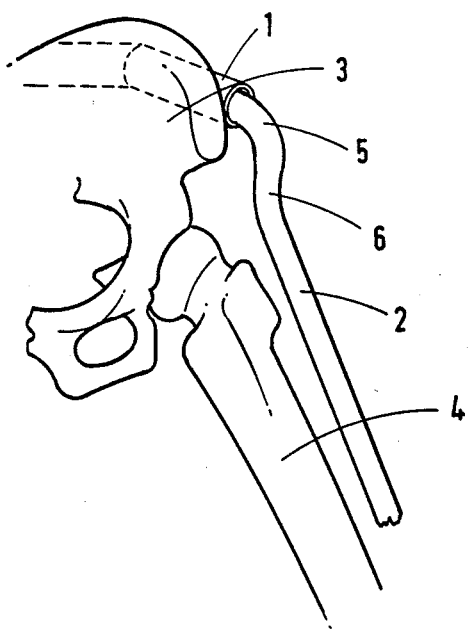

FIG. 1 shows the relationship of the sleeve (1) and leg bar (2) of one side of the device of the present invention to the pelvis (3) and femur (4) respectively. The leg bar (2) has two bends (5, 6) near the end which is held by the sleeve (1). The first bend (5) is of a simple angle and the second bend (6) is of a compound angle and is made so that the major portion of the leg bar (2) lies parallel to the femur (4).

Figure 2:
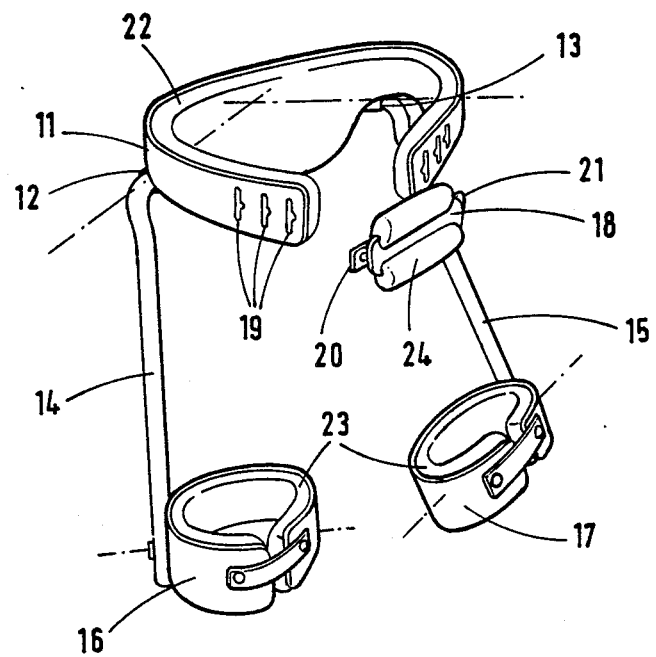
FIG. 2 shows the position of the device in hip extention.

In FIG. 2 the device is shown as it would be when worn when the hips are in extension. The device comprises a waist band (11) having attached to its outside two sleeves (12, 13) which are inclined downwards and their axes intersect to form an angle as shown by the dotted lines on the waist band. The two leg bars (14, 15) are held in the sleeves (12, 13) at one end, the other end of the leg bars carry thigh bands (16, 17) which fit around the thighs of the wearer. The thigh bands (16, 17) are free to rotate about an axis shown by the dotted line at the thigh bands. The thigh bands may be adjusted around the leg bars (14, 15) using a locking nut (not shown) to adjust for an individual wearer or variation in downward inclination of the sleeve. In use the thigh bands (16, 17) are locked to prevent rotation about the leg bars (14, 15). The waist band carries an anterior pressure pad (18) which engages with the waist band (11) in holes which may be slots (19) or circular holes.

The waist band (11) may carry a number of holes (19) so that it may be tightened or loosened as required. The anterior pad (18) may possess lugs (20, 21) which engage into holes (19). The waist band (11), thigh band (16, 17) and anterior pressure pad (18) may be lined with a resilient material (22, 23, 24). The resilient material may be conventional non-woven surgical padding material or a foam, particularly a polyurethane foam.

Figure 3:
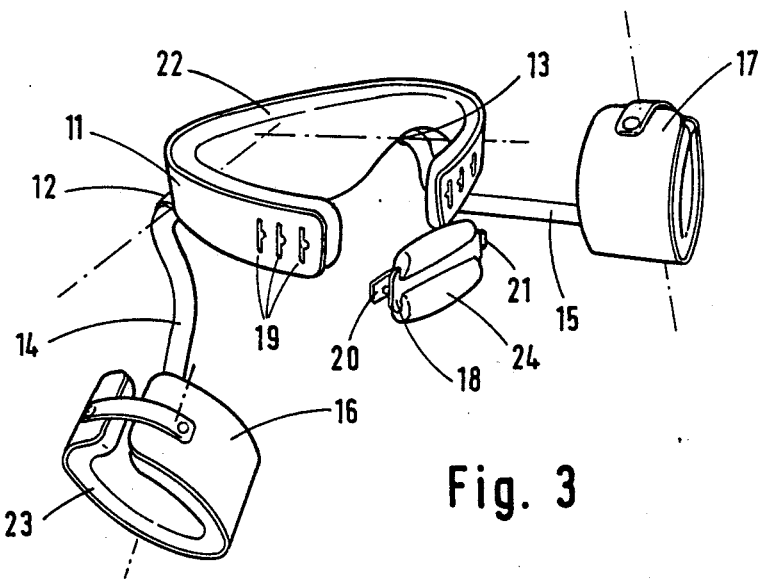
FIG. 3 shows the position of the device in hip flexion.

FIG. 3 shows the device of FIG. 2 in a position where the hip is in flexion. There is an increase in leg abduction which results from the rotation of the leg bars (14, 15) about the inclined axis of their sleeves (12, 13). The thigh bands (16, 17) have also rotated to a more anterior position.

Figure 4:
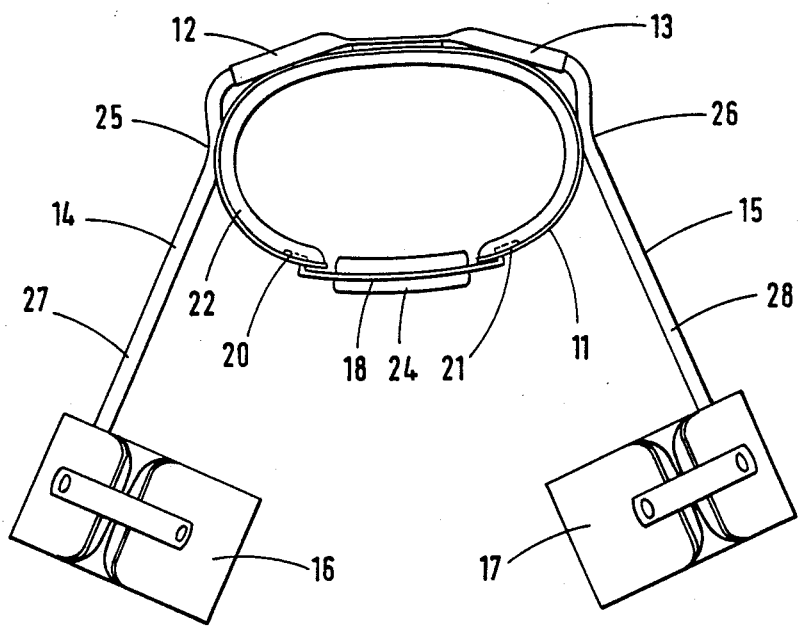
FIG. 4 shows a diagrammatical view of the device from above.

FIG. 4 shows a diagrammatical view of the device of FIG. 3 from above. The waist band (11) is shown with the anterior pressure pad (18) in position. This is a fixed position with the lugs (20, 21) fitted through the holes. The bends (25, 26) are shown in the leg bars (14, 15) so that the major portion of the leg bars (27, 28) lies substantially parallel to the leg when worn. The thigh bands (16, 17) are shown at one end of the leg bars (14, 15). The other end of the leg bars are held in sleeves (12, 13) which are in turn attached to the waist band (11). The sleeves (12, 13) are shown angled forward.

Figure 5:
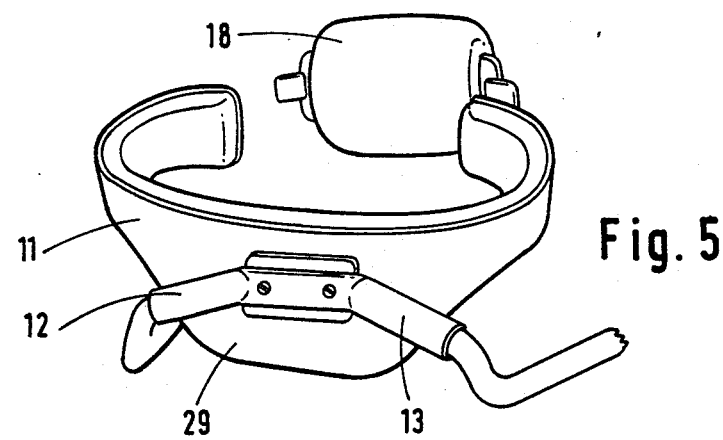
FIG. 5 shows a rear view of the waist band with fixed sleeves.

FIG. 5 shows a rear view of the waist band (11) and the anterior pressure pad (18). The waist band (11) has a posterior expansion (29) which prevents rotation of the device and increases the area of contact with the sacrum thereby increasing the comfort in wearing the device. The posterior expansion (29) and the anterior pressure pad (18) act together to maintain the waist band (11) more or less parallel to the coronal plane. The muscles of adduction and internal rotation tend to draw the leg bars together particularly during hip flexion. This force when transmitted to the waist band tends to tilt it backwards, this is over come by upward pressure on the posterior expansion (29) and downward pressure on the anterior pressure pad (18). The sleeves (12, 13) are shown having a downward inclination. The sleeves (12, 13) are fixed in one position in this particular embodiment as shown by the screws and plate.

Figure 6:
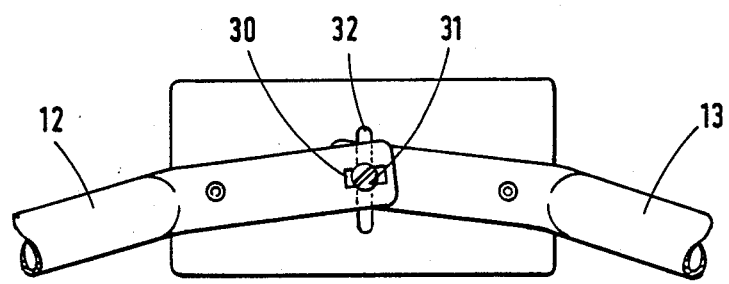
FIG. 6 shows a form of varying the inclination of the sleeves.

FIG. 6 shows one means of allowing the angle of downwards inclination of the sleeves (12, 13) to be varied. Each sleeve carries a horizontal slot (30) through which passes a fixation bolt (31) which is able to move vertically in slot (32) but which can be tightened to hold each sleeve (12, 13) in a given inclined configuration.

Figure 7:
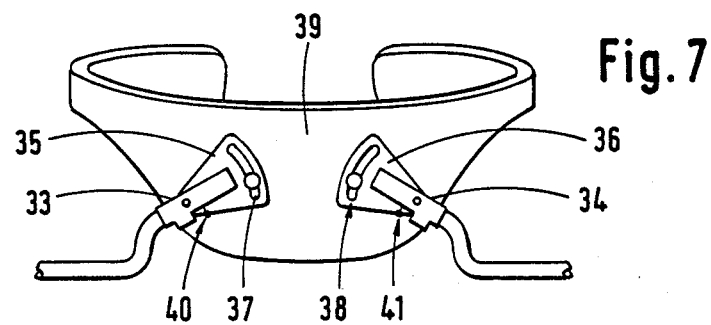
FIG. 7 shows an alternative means of varying the inclination of the sleeves.

FIG. 7 shows a second means altering the inclination of the sleeve (33, 34) which may be individually altered. The sleeves (33, 34) are attached to plates (35, 36) which each contain an arcuate slot (37, 38) in which there is a fixing bolt which passes through to a reinforcing plate (not shown) of the waist band (39). To alter the inclination of each sleeve (33, 34), the fixing bolt is loosened, the plate rotated to the new position and the fixing bolt retightened. A spring clip (40, 41) may be used to interact in a groove in the leg bar to retain the leg bar in the sleeve. By having more than one groove in each leg bar, the separation of the leg bars may be altered by selecting a different groove.

Figure 8:
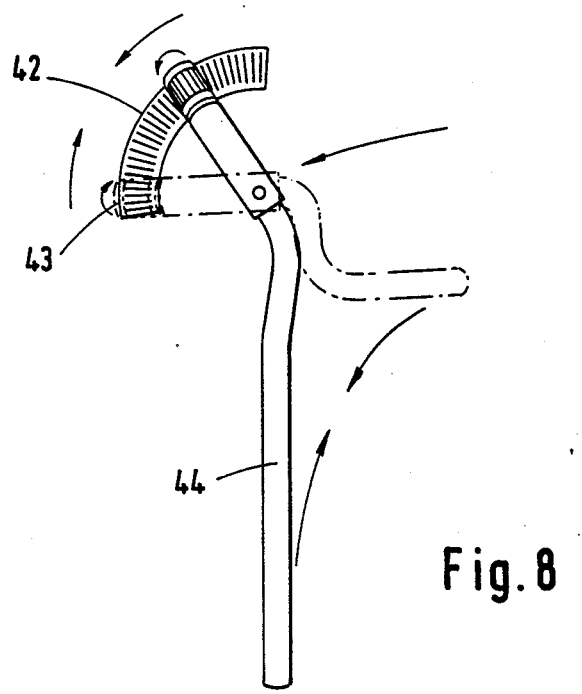
FIG. 8 shows a further means of varying the inclination of the sleeves.

FIG. 8 shows an alternative means of variation of the inclination of the sleeve means. In this embodiment the inclination of the sleeve varies continually as the sleeve rotates about an axis perpendicular to it. When the hip is extended the sleeve axis is inclined downwards in a manner shown in FIG. 2. However, in this embodiment a pinion (43) at the end of the leg bar (44) engages a rack (42) on the waist band and the pinion (43) moves the pivot axis towards the horizontal during hip flexion. When the hips are fully flexed, the sleeve is horizontal and the leg bars overcome adductor tone without any further input of work from the wearer.

Figure 9:
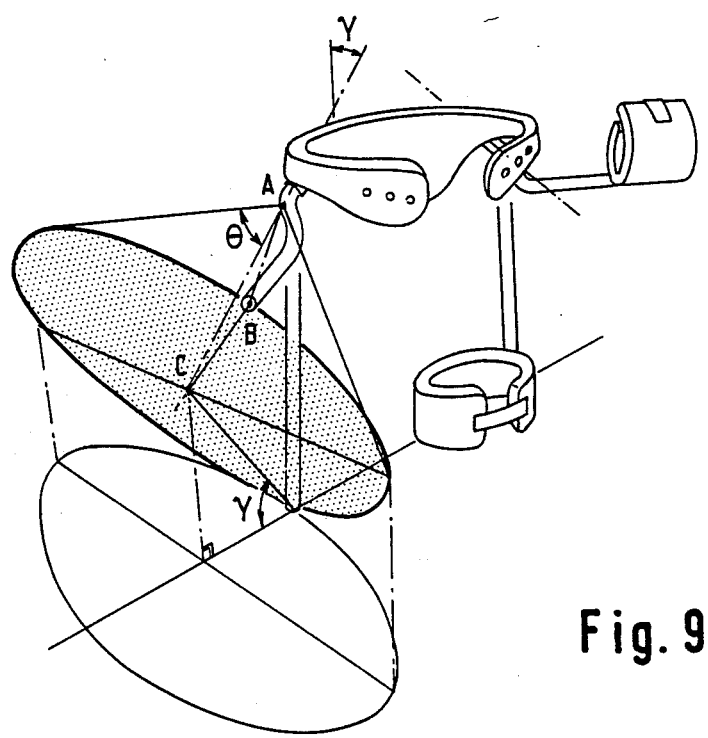
FIG. 9 illustrates diagrammatically the abduction caused by rotation of the leg bar about the inclined sleeve axis.

In FIG. 9 the sleeve axis represented by the line AC is inclined at an angle $\gamma$ from the vertical. The angle $\gamma$ may be varied using one the means illustrated in FIGS. 6, 7 or 8. The line AB joins the first bend of the leg bar to its tip. $\theta$ is the angle between the line AB and the sleeve axis AC. When rotated about AC the end B of the leg bar describes the circular base of an inclined cone. The horizontal reflection of that circle is an ellipse and leg abduction, which occurs in the horizontal plane, may be calculated by the reflection of the tip of the leg bar onto that ellipse.

I claim:

1. An orthopaedic device which comprises a waist band, two thigh bands and two leg bars in which one end of each of the leg bars is attached to a thigh band which is free to rotate about an axis perpendicular to the leg bar, the other end of each leg bar being freely rotatable about its axis and being held for rotation within a sleeve attached to the waist band, each sleeve being capable of being inclined downwards with respect to the plane of the waist band; and said leg bars make an obtuse angle with the axis of the sleeve whereby when worn the separation of leg bars is less when the legs are extended than when they are flexed and in which each leg bar is adapted so that when worn each leg bar is parallel to the leg of the wearer.

2. A device according to claim 1 in which the angle at which the sleeve is inclined downwards is invariable.

3. A device according to claim 1 in which the angle at which the sleeve is inclined downwards is variable.

4. A device according to claim 3 in which the angle at which each of the sleeves is inclined downwards is independently variable with respect to each other.

5. A device according to claim 3 in which the axis of rotation of the thigh bands may be altered by rotation of the thigh band around the leg bar.

6. A device according to claim 1 in which the sleeve is angled forward.

7. A device according to claim 6 in which the leg bar has plurality of circumferential grooves in a portion which is present within the sleeve and is held in the sleeve by means of a spring clip which registers in one of the grooves.

8. A device according to claim 1 in which the leg bars may be reversibly locked against rotation in their sleeves whereby in use the device then acts as a splint.

9. A device according to claim 1 in which the leg bars have restricted rotation within their sleeves.

10. A device according to claim 1 in which the waist band includes a separable anterior pressure pad.

11. A device according to claim 1 in which the sleeve is capable of being inclined downwards at an angle which is continuously variable.

* * * * *